US011634456B2

(12) United States Patent
Mearns Spragg (10) Patent No.: US 11,634,456 B2
(45) Date of Patent: Apr. 25, 2023

(54) METHOD FOR THE PURIFICATION OF COLLAGEN (71) Applicant: JELLAGEN PTY LTD, Stirling (GB)

(72) Inventor: Andrew Mearns Spragg, Central Scotland (GB)

(73) Assignee: JELLAGEN PTY LTD, Stirling (GB)

( * ) Notice: Subject to any disclaimer, the term of this patent is extended or adjusted under 35 U.S.C. 154(b) by 289 days.

(21) Appl. No.: 16/618,439

(22) PCT Filed: Jun. 1, 2018

(86) PCT No.: PCT/GB2018/051506
§ 371 (c)(1),
(2) Date: Dec. 2, 2019

(87) PCT Pub. No.: WO2018/220396
PCT Pub. Date: Dec. 6, 2018

(65) Prior Publication Data
US 2021/0139533 A1    May 13, 2021

(30) Foreign Application Priority Data

Jun. 2, 2017 (GB) .................................. 1708853

(51) Int. Cl.
C07K 1/14 (2006.01)
A61L 15/32 (2006.01)
C07K 1/34 (2006.01)
C07K 14/78 (2006.01)
C12N 5/00 (2006.01)

(52) U.S. Cl.
CPC ............ C07K 1/145 (2013.01); A61L 15/325 (2013.01); C07K 1/34 (2013.01); C07K 14/78 (2013.01); C12N 5/0062 (2013.01)

(58) Field of Classification Search
CPC ....... G01N 2001/4083; G01N 2333/78; A61K 35/35; C07K 1/145; C07K 1/34; C07K 14/78; A61L 15/325; A61L 27/24; A61L 27/56
See application file for complete search history.

(56) References Cited

U.S. PATENT DOCUMENTS

| 3,131,130 | A |   | 4/1964 | Oneson | |
|---|---|---|---|---|---|
| 4,242,291 | A | * | 12/1980 | Hughes | A61L 15/325 |
| | | | | | 264/1.21 |
| 6,204,365 | B1 | * | 3/2001 | Devore | A61F 9/00819 |
| | | | | | 128/858 |
| 2003/0204023 | A1 | * | 10/2003 | Koob | C08L 2666/02 |
| | | | | | 525/242 |
| 2004/0253678 | A1 | * | 12/2004 | Hsiao | C07K 14/78 |
| | | | | | 435/69.1 |
| 2007/0151925 | A1 | * | 7/2007 | de los Reyes | B01D 63/02 |
| | | | | | 210/641 |
| 2011/0288026 | A1 |   | 11/2011 | Simpson et al. | |
| 2012/0003230 | A1 | * | 1/2012 | Trogden | A61K 39/3955 |
| | | | | | 424/142.1 |
| 2012/0273993 | A1 | * | 11/2012 | Shoseyov | A61L 27/24 |
| | | | | | 264/202 |
| 2012/0302734 | A1 | * | 11/2012 | Sutherland | C07K 14/43572 |
| | | | | | 530/353 |
| 2013/0071645 | A1 | * | 3/2013 | Park | A61L 27/24 |
| | | | | | 428/318.6 |
| 2013/0251750 | A1 | * | 9/2013 | Sim | A61K 9/0019 |
| | | | | | 424/272.1 |
| 2014/0147400 | A1 | * | 5/2014 | Bakar | C07K 14/78 |
| | | | | | 424/59 |
| 2017/0204136 | A1 | * | 7/2017 | Dhara | C08L 5/08 |

FOREIGN PATENT DOCUMENTS

| EP | 0284789 | 10/1988 |
|---|---|---|
| EP | 3222299 | 9/2017 |
| KR | 2014-0122532 | 10/2014 |
| WO | WO 1997/042986 | 11/1997 |
| WO | WO 2004/090151 | 10/2004 |
| WO | WO 2010/048281 | 4/2010 |
| WO | WO 2016/080578 | 5/2016 |

OTHER PUBLICATIONS

Catalina et al. (2013) Molecular weight separation of collagen-base biomaterials by ultrafiltration, pp. 1-6.*
Evidence for the publication date for "Catalina et al." (ref "U") Molecular weight separation of collagen-base biomaterials by ultrafiltration (2013) pp. 1-12.*
Millipore_TFF (2008) Protein Concentration and Diafiltration by Tangential Flow Filtration, pp. 1-24.*
Addad et al. (2011) Isolation, Characterization and Biological Evaluation of Jellyfish Collagen for Use in Biomedical Applications, Mar. Drugs, vol. 9, pp. 967-983.*
Merckmillipor (2014) Sample preparation product guide, pp. 1-250.*
Liu et al., "Effects of alkaline pretreatments and acid extraction conditions on the acid-soluble collagen from grass carp (*Ctenopharyngodon idella*) skin," Food Chemistry, 172:836-843, 2014.
PCT International Search Report issued in International Application No. PCT/GB2018/051506, dated Nov. 6, 2018.
Schmidt et al., "Collagen extraction process," *International Food Research Journal*, 23(3):913-922, 2016.

(Continued)

*Primary Examiner* — Iqbal H Chowdhury
(74) *Attorney, Agent, or Firm* — Parker Highlander, PLLC (57) ABSTRACT

A process for the extraction of collagen from collagen-containing matter, wherein the process comprises; incubating the collagen-containing matter in an acidic solution to form an incubant, then diafiltrating the incubant to substantially purify solubilised collagen within the incubant, thereby forming a retentate, then separating the soluble and insoluble matter of the retentate to remove the remaining insoluble matter, wherein the soluble matter is a substantially pure collagen solution.

10 Claims, 5 Drawing Sheets

(56) References Cited

OTHER PUBLICATIONS

Silver and Trelstad, "Type I collagen in solution. Structure and properties of fibril fragments," *J. Biol. Chem.*, 255(19):9427-9433, 1980.

Jellagen "Jellyfish Collagen Biomaterials Next Generation Collagen for Cell Culture and Med-Tech Products", Overview Presentation, Feb. 11, 2016.

* cited by examiner

Figure 5

METHOD FOR THE PURIFICATION OF COLLAGEN

This application is a national phase application under 35 U.S.C. § 371 of International Application No. PCT/GB2018/051506, filed Jun. 1, 2018, which claims the benefit of United Kingdom Patent Application No. 1708853.5, filed Jun. 2, 2017, the entirety of each of which is incorporated herein by reference.

FIELD OF INVENTION

The invention relates to a novel process for the purification of collagen and the collagen obtainable therefrom.

BACKGROUND OF THE INVENTION

Tissue engineering offers the exciting potential to overcome the limitations of organ transplantation by providing man-made tissues and organs to patients desperately in need of them. Standard tissue engineering techniques first require the culturing of autologous or immune-compatible cells within three-dimensional polymers in vitro, prior to transplanting the cells into the patient to stimulate development of the desired tissue or organ.

The polymer scaffold is essential to this process by controlling the initial development of the naïve tissue to a defined three-dimensional structure. The scaffold also controls the functional development of the tissue in vivo by acting as a surrogate extracellular matrix until the cells adequately form an extracellular matrix (ECM) of their own (Agrawal & Ray, 2001). The ECM is essential for controlling the diffusion of nutrients, metabolites and soluble factors to ensure the desired tissue develops at the site of transplantation.

There is also a need to develop three-dimensional scaffolds suitable for in vitro tissue engineering, rather than simply mediating tissue regeneration in vivo. The challenge of tissue engineering is the creation of an optimised scaffold for this role.

Until now, most of the effort has focused on developing polymer scaffolds using biodegradable and biocompatible polymers. An ideal tissue engineering scaffold as a surrogate of the native ECM should mimic the native ECM at both the structural and compositional level. Collagen is one of the predominant components of the ECM.

Collagen is a highly-valued biomaterial that is used in the pharmaceutical and medical device industry. Collagens are a structurally similar group of proteins of which at least 28 different types (designated as types I to XXVII) exist (Birk and Bruckner, 2005). They function as a substantial component of the extracellular scaffold and have thrombotic and haemostatic properties. Collagens contribute 20-30% of total mammalian protein content (Harkness, 1961).

Due to their ubiquity in mammalian physiology, collagens have a variety of applications and a long history of clinical use. When used as a biomaterial their ability to encourage cell adhesion, naturally degrade into harmless byproducts which are reabsorbed, and possession of low immunoreactivity and low toxicity (Friess, 1998; Maeda et al., 1999, Bakar et al., 2011) has led to their use in wound dressings and other applications where tissue remodelling or structural healing is achieved by collagen functioning as an artificial extra cellular matrix (ECM) for cells to populate.

Collagen is thus an ideal polymeric species for enabling the propagation of autologous cells in vitro prior to reinfusion into the patient to stimulate the development of the desired tissue or organ in vivo.

Due to this proven utility, processes have been developed for the purification of collagen at an industrial scale. However these purification processes often involve subjecting the collagen to harsh environmental and mechanical stresses that damage the native fold of the molecule. The lack of a native-like conformation decreases the malleability of the purified collagen product and thus precludes the construction of three-dimensional scaffolds that accurately mimic the dimensions of the tissue that requires engineering. This is evidently a barrier to enabling the generation of useful tissues entirely in vitro.

Thus, there is a need to improve collagen purification processes to enable the extraction of collagen in a conformation more desirable for the manufacture of three-dimensional collagen scaffolds.

Electrospinning is a fibre production method which uses electric force to draw charged threads of polymer solutions or polymer melts up to fibre diameters in the order of some hundred nanometers. Electrospinning shares characteristics of both electrospraying and conventional solution dry spinning of fibres. The process does not require the use of coagulation chemistry or high temperatures to produce solid threads from solution. This makes the process particularly suited to the production of nano scale fibres using large and complex molecules including collagen.

Although a number of previous articles have referred to the ability to electrospin collagen (Matthews J. A et al. 2002; Rho et al 2006; Chakrapani V Y et al. 2012; To date, collagen nanofiber production utilizes hexafluoro isopropanol (HFIP) or TFE as a solvent for electrospinning. This results in the denaturation of the collagen.

Thus there is a need to both improve the processes to extract collagen and produce collagen which can retain its structure in the production of three-dimensional scaffolds.

SUMMARY OF THE INVENTION

This invention is predicated on the unexpected discovery that significant improvements to the efficiency of collagen extraction can be achieved by using diafiltration. Further by performing an additional filtration step during a collagen extraction process enables the efficient purification of monomeric collagen. The monomeric collagen exhibits advantageous properties when polymerised into higher-order collagen scaffolds.

Standard collagen extraction processes use a combination of filtration, salting and centrifugation to isolate collagen. However, the use of centrifugation in the extraction process can introduce limitations into the volume of collagen that can be processed and the time needed to process the collagen. As such the centrifugation stage may be considered a rate limiting step in the collagen extraction process. Standard filtration methods are also problematic in the collagen extraction, due to a unique characteristic of collagen molecules to lie flat against the membrane filter, which results in blocking and membrane fouling.

The present invention is based on the observation that the use of diafiltration methods, in which the membrane is perpendicular to the flow of the retentate, provides an improved collagen extraction process over those which utilise centrifugation. This improved extraction process allows large quantities of collagen to be processed and in a shorter time frame. Further the combination of this extraction process with an additional filtration step allows the efficient purification of monomeric collagen.

Monomeric collagen produced from the method of the present invention has been shown to have excellent qualities for electrospinning to form three-dimensional structures. For example the monomeric collagen has improved solubility and can be electrospun using benign solvents. Further it has surprisingly ben found that the collagen extracted by the method of the present invention can retain its monomeric structure after being electrospun.

Accordingly, in a first aspect of the invention, there is a process for the extraction of collagen from collagen containing matter, comprising the steps of: (a) incubating the collagen-containing matter in an acidic solution for at least 1 h at a temperature in the range of about 4° C. to about 37° C. to form an incubant; (b) diafiltrating the incubant from step (a) to substantially purify solubilised collagen within the incubant, thereby forming a retentate; (c) separating the soluble and insoluble matter of the retentate obtained from step (b) to remove the remaining insoluble matter; and (d) optionally repeating steps (a) and (b) on the remaining insoluble matter, wherein the soluble matter obtained from step (c) is a substantially pure collagen solution.

According to a second aspect of the invention, there is provided an isolated monomeric collagen obtainable by the process of the first aspect of the invention.

According to a third aspect of the invention, there is provided a kit comprising the isolated collagen produced according to the first aspect of the invention and a gelling catalyst, said gelling catalyst being an aqueous solution with a pH in the range of from about pH 4 to about pH 9.

According to a fourth aspect of the invention, there is a process for the production of a three-dimensional collagen matrix scaffold comprising the steps of: (a) preparing a monomeric collagen spinning solution by: (i) lyophilising the monomeric collagen solution according to the first aspect of the invention or the collagen obtainable from the process of the second aspect of the invention; (ii) dissolving the lyophilised monomeric collagen in an organic solvent; and (b) spinning the spinning solution by using an electrospinner and volatilizing the organic solvent at the same time to form a 3D collagen scaffold.

According to a fifth aspect of the invention, there is provided a three-dimensional collagen scaffold obtainable by electrospinning the collagen of the first aspect of the invention or the collagen obtainable by the process of the second aspect of the invention.

According to a sixth aspect of the invention, there is provided a three-dimensional collagen scaffold obtainable by the process of the fourth aspect of the invention.

According to a seventh aspect of the invention, there is provided an electrospun collagen scaffold characterised in having a relative peak ratio of at least 1.05, wherein the greatest peak intensity in a peak region of 1670 $cm^{-1}$ or less and 1630 $cm^{-1}$ or more in an FTIR spectrum is the denominator, and the greatest peak intensity in the peak region of 1575 $cm^{-1}$ or less and 1515 $cm^{-1}$ or more in an FTIR spectrum is the numerator.

LIST OF DRAWINGS

The invention is illustrated by reference to the following drawings, in which.

DETAILED DESCRIPTION OF THE INVENTION

Accordingly, in a first aspect of the invention, there is a process for the extraction of collagen from collagen containing matter, comprising the steps of: (a) incubating the collagen-containing matter in an acidic solution for at least 1 h at a temperature in the range of about 4° C. to about 37° C. to form an incubant; (b) diafiltrating the incubant from step (a) to substantially purify solubilised collagen within the incubant, thereby forming a retentate; (c) separating the soluble and insoluble matter of the retentate obtained from step (b) to remove the remaining insoluble matter; and (d) optionally repeating steps (a) and (b) on the remaining insoluble matter, wherein the soluble matter obtained from step (c) is a substantially pure collagen solution.

According to the first aspect of the invention, the process involves incubating the collagen-containing matter in an acidic solution for at least 1 h at a temperature in the range of about 0° C. to about 37° C. to form an incubant. This is referred to as step (a) of the process.

The purpose of step (a) is to solubilise the collagen contained within the collagen-containing matter. In some embodiments, step (a) is performed at a temperature in the range of about 2° C. to about 6° C. An "acidic solution" is any solution with a pH of 5.0 or less, pH of 4.5 or less, pH 4.0 or less, pH 3.5 or less, pH 3.0 or less, or pH 2.0 or less. In some embodiments, step (a) is performed by incubating the collagen-containing matter in a 0.2 M, 0.3 M, 0.4 M, 0.5 M, 0.6 M, 0.7 M, 0.8 M, 0.9 M or 1 M acid. Although the skilled person would understand that the acid is not a limiting feature of the invention, the acid may be, by way of example, acetic acid, for example 0.5 M acetic acid.

Step (a) is performed for at least 1 h, meaning that, prior to proceeding to step (b) of the process, the collagen-containing matter is incubated in the acidic solution for at least 1 h. In some embodiments, step (a) is performed for in the range of 1 h to 168 h, whereby increasing the incubation time increases the amount of collagen that is solubilised during step (a). In some embodiments, step (a) is performed for 72 h.

During step (a), the solution may be agitated, for example, by continuously stirring the solution at, for example, 200 rpm. Constant agitation ensures efficient mixing of the solution to increase the efficiency of the collagen solubilisation. The preferred time for which step (a) is to be performed will be dependent of several other features of the invention, for example, the concentration of the acid solution and temperature at which step (a) is performed. Trial and error associated with determining the optimal parameters for each of the inter-related features is within the capabilities of the skilled person.

As used herein, the phrase "collagen-containing matter" refers to a source material from which the collagen is to be extracted. In some embodiments, the collagen-containing matter is derived from an organism selected from the list consisting of jellyfish, anemone, echinoderms, limpets, mussels, sea cucumbers, bovine, porcine, rodent, equine or finfish. In some embodiments the collagen-containing matter is derived from jellyfish. The jellyfish may be selected from the list consisting of *Rhizostomas pulmo, Rhopilema esculentum, Rhopilema nomadica, Stomolophus meleagris, Aurelia* sp., *Nemopilema nomurai* and a combination thereof.

In some embodiments, the collagen-containing matter is derived from a sea cucumber, preferably wherein the sea cucumber is *Stichopus mollis*.

In some embodiments, the collagen-containing matter is derived from a mussel, preferably wherein the mussel is *Mytilus edulis*.

In some embodiments, the collagen-containing matter is derived from a limpet, preferably wherein the limpet is *Patella vulgate*.

In some embodiments, the collagen-containing matter is derived from an echinoderm, preferably wherein the sea urchin is *Echinus esculentus*.

In some embodiments, the collagen-containing matter is derived from bovine. For example, the collagen may be derived from bovine skin and/or tendon.

Further to step (a), the process involves diafiltrating the incubant from step (a) to substantially purify solubilised collagen within the incubant thereby forming a retentate. The purpose of this step is to purify solubilised collagen from the hydrolysed non-collagenous material. This is referred to as step (b) of the process.

It has herein been found that the use of diafiltration substantially improves the efficiency of the collagen extraction process. The terms "diafiltration", "diafiltrating" or "diafiltering" would be understood by the person skilled in the art to refer to a technique that uses ultrafiltration membranes to completely remove, replace, or lower the concentration of salts, solvents and/or acid hydrolysed material from solutions containing proteins, peptides, nucleic acids, and other biomolecules. In a preferred embodiment the diafiltration method used is tangential flow filtration more preferably hollow fibre membrane filtration.

As used herein, the term "incubant" refers to the solution obtained after completion of step (a) of the process. The incubant may comprise a mixture of solubilised collagen and insoluble matter. The incubant is diafiltered for a sufficient time to substantially purify the collagen from the salts or solvents, where the collagen is "substantially" pure when the salts or solvents comprise less than 2 wt % of the diafiltrate (i.e. the "retentate"). The sufficient time can be determined, for example, by constant sampling of the retentate to determine when the wt % salt content is below or equivalent to the value of 2 wt % of the total wt % of solution. In some embodiments, step (b) is performed using a hollow fibre membrane with a molecular weight cut-off of 50 kDa.

The first aspect of the invention may further involve separating the soluble and insoluble matter of the retentate obtained from step (b) to remove residual insoluble matter. The residual insoluble matter may comprise non-solubilised collagen. The soluble matter obtained from this step is a substantially pure collagen solution. This is referred to as step (c) of the process. In some embodiments, step (c) is performed by filtration or chromatography. In some embodiments, step (c) is performed by filtration. The filtration may be performed by passing the retentate through a filter having a pore size of 1 μm or 20 μm. The filter may be of hollow fibre or ceramic composition.

Step (d) of the process is an optional feature involving the repetition of steps (a) and (b) on the remaining insoluble matter obtained from step (c).

In some embodiments, the process further comprises passing the substantially pure collagen solution obtained from step (c) of the process through one or more filters having a pore size selected from the list consisting of 0.1 μm 0.2 μm, 0.3 μm, 0.4 μm, 0.5 μm 0.6 μm, 0.7 μm, 0.8 μm and a combination thereof. The inventors have found that the addition of a filtration step after the extraction of the substantially pure collagen solution enables the purification of the collagen based on its conformational properties.

In some embodiments, the substantially pure collagen solution is filtered through a 0.4 μm filter, and the filtrate obtained is a mixture of a substantially pure solution comprising monomeric collagen and beta collagen. The substantially pure solution comprising monomeric collagen and beta collagen may be further passed through a filter having a pore size of 0.2 μm, where the filtrate is a substantially pure solution of monomeric collagen.

In some embodiments, the substantially pure collagen solution of step (c) is passed through a filter having a pore size of 0.2 μm, where the filtrate is a substantially pure solution of monomeric collagen.

In some embodiments, prior to step (a), the collagen-containing matter may undergo a pre-treatment step of incubating the collagen-containing matter in a strong base for from 4 h to 96 h at a temperature in the range of from 2° C. to 37° C. This is referred to as step (i) in the process. The pre-treatment step (i) hydrolyses non-collagenous material within the collagen-containing matter, thereby increasing the purity of the final collagen solution. In some embodiments, the strong base is a 0.1, 0.2 M, 0.3 M, 0.4 M, 0.5 M, 0.6 M, 0.7 M, 0.8 M, 0.9 M or 1 M sodium hydroxide solution.

After step (i), the process further comprises diafiltering the incubant of step (i) to remove the dissolved non-collagenous material and retaining the retentate for use in step (a) of the process. These steps are referred to as steps (ii) and (iii), respectively.

Further to the surprising molecular characteristics of the collagen obtainable from the process defined by the third aspect of the invention, the inventors have surprisingly found that the collagen obtained from this process has surprisingly superior aggregation properties compared to the isolated collagens of the art.

According to a second aspect of the invention, there is provided an isolated monomeric collagen obtainable by the process of the first aspect of the invention.

As defined herein, the term "isolated" refers to a naturally derived molecule substantially purified and/or free-from the constituents of its native environment. The present invention relates to an "isolated" monomeric collagen. The monomeric collagen obtained from the process of the invention is particularly advantageous for forming three-dimensional collagen scaffolds in comparison with isolated collagens of the art, which are purified as higher-order polymeric structures.

In some embodiments, the isolated monomeric collagen obtainable by the process of the invention will be in the range of about 50 kDa to about 200 kDa. The exact mass of the collagen will be dependent upon the source from which the collagen is to be purified and the isoform of collagen to be purified. So far, 28 types of collagen have been described. For the purposes of the present invention the exact isoform of collagen is not limiting. There are numerous methods available in the art for determining the molecular mass of polypeptides, which include, but not limited to, size exclusion chromatography, electrospray ionisation (ESI) mass spectrometry and SDS polyacrylamide gel electrophoresis (SDS PAGE).

The collagen may be in a native or non-native conformation. A "non-native" conformation refers to a collagen that is predominantly unfolded and thus devoid of substantial elements of secondary or tertiary structure. In some embodiments, the isolated monomeric collagen of the invention is in a native conformation, where "native" means that the collagen polypeptide is in a predominantly folded three-dimensional conformation comprising secondary structural elements such as alpha helices and beta-sheets. The native conformation may be a three-dimensional structure that is biologically functional in vivo. The native confirmation may be the in vivo three-dimensional structure of the monomeric collagen. The native conformation may be the in vivo native conformation of a collagen subunit when assembled within a higher order collagen structure. Alternatively, the native conformation may not be a three-dimensional structure found in vivo, but nevertheless be a conformation that retains secondary structural features. Examples of methods that can be used to determine the conformation of a polypeptide include, but are not limited to, solution state-NMR, native page analysis, Raman spectrometry, ESI-mass spectrometry (ESI-MS) and Fourier transform IR spectroscopy (FTIR). For example, soft ionisation mass spectrometry techniques such as ESI-MS can determine the folded or unfolded state of a polypeptide by determining the number of charges that adduct to the side chains of amino acids during the ionisation process. As, in general, fewer amino acids are in a solvent-accessible conformation when a polypeptide is in a native, compact conformation, the number of charges adducted to a polypeptide will be lower. The number of adducted charges can be determined from analysing the mass-to-charge spectrum obtained from the sample under analysis.

Another technique, FTIR, can be used to obtain an infrared spectrum of the absorption at a range wavelengths of infrared light of a polypeptide. Different secondary structural elements differentially absorb particular wavelengths of infrared light. Thus determining the IR absorption pattern of a polypeptide can provide information as to its conformational properties. The conformation-dependent absorption properties of polypeptides are derived from the hydrogen bonding pattern of the amide groups of the peptide bonds covalently linking the amino acid subunits that make up the polypeptide chain. When present within alpha helices, the polypeptide backbone is coiled into a right-handed helix, where hydrogen bonding occurs between amides located on successive turns in a helix. Conversely, when present within a beta-sheet, hydrogen bonds form between amide of amino acids separated over a much greater length of the polypeptide sequence. The different packaging constraints of secondary structural features give rise to distinct C=O and N—H bond stretch vibrational frequencies which manifest as distinct absorption patterns in the following so-called amide regions of an FTIR spectrum: the amide I region, between 1700 to 1600 $cm^{-1}$, the amide II region, between 1480 to 1575 $cm^{-1}$, and the amide III region, between 1229 to 1301 $cm^{-1}$. The apparent absorption of IR light in each of these regions, or lack thereof, can be used to determine the secondary structural content of a polypeptide.

In some embodiments, the isolated monomeric collagen obtainable by the process of the invention has a relative peak ratio of at least 1.05, wherein the greatest peak intensity in a peak region of 1670 $cm^{-1}$ or less and 1630 $cm^{-1}$ or more in an FTIR spectrum is the denominator of the relative peak ratio, and the greatest peak intensity in the peak region of 1575 $cm^{-1}$ or less and 1515 $cm^{-1}$ or more in an FTIR spectrum is the numerator of the relative peak ratio. The inventors have surprisingly found that the collagen extracted using the process of the invention displays a greater greatest peak intensity in the amide II region of an FTIR spectrum in comparison to the amide I region of the same FTIR spectrum. Hence, the collagen of the invention has a relative peak ratio of at least 1.05. This is converse to the relative peak ratios of the collagen comprised in the state of the art. Without wishing to be bound by theory, the inventors believe that the increase in peak intensity in the amide II region of the spectrum for the collagen disclosed herein is due to the reduced presence of the collagen triple helix due to the reduced presence of collagen quaternary structure. As the presence of triple helix structure manifests in an absorption in the amide I region of the spectrum, the absence of some or all triple helix structure reduces the peak intensity in the amide I region of the FTIR spectrum.

Figure 2:
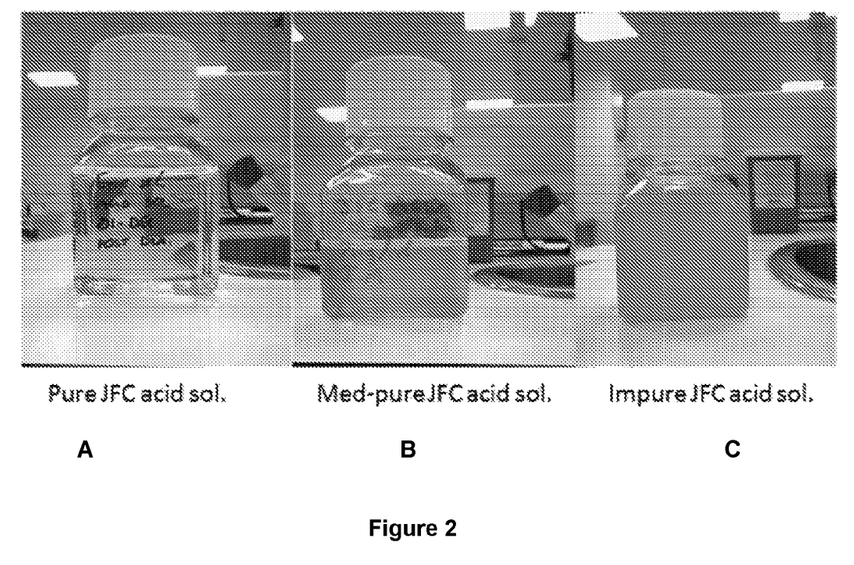
FIG. 2 shows images of collagen samples throughout the purification process. Panel A contains collagen purified by the method disclosed herein. Panel C contains the collagen staring material before purification.
Figure 3:
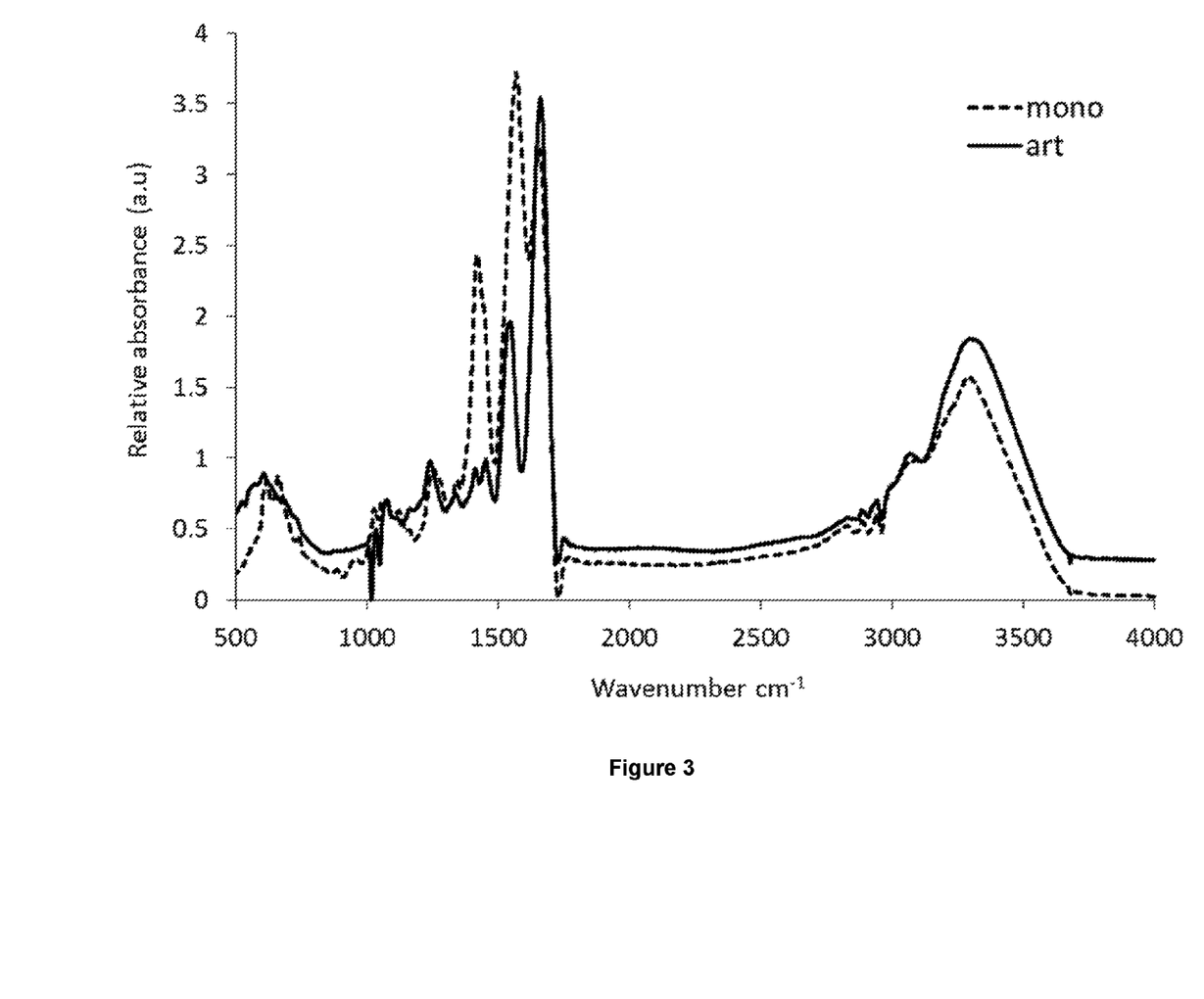
FIG. 3 shows the FTIR spectrum of jellyfish collagen either extracted using the process of the invention (mono) or extracted using methods of the art (art).
Figure 4:
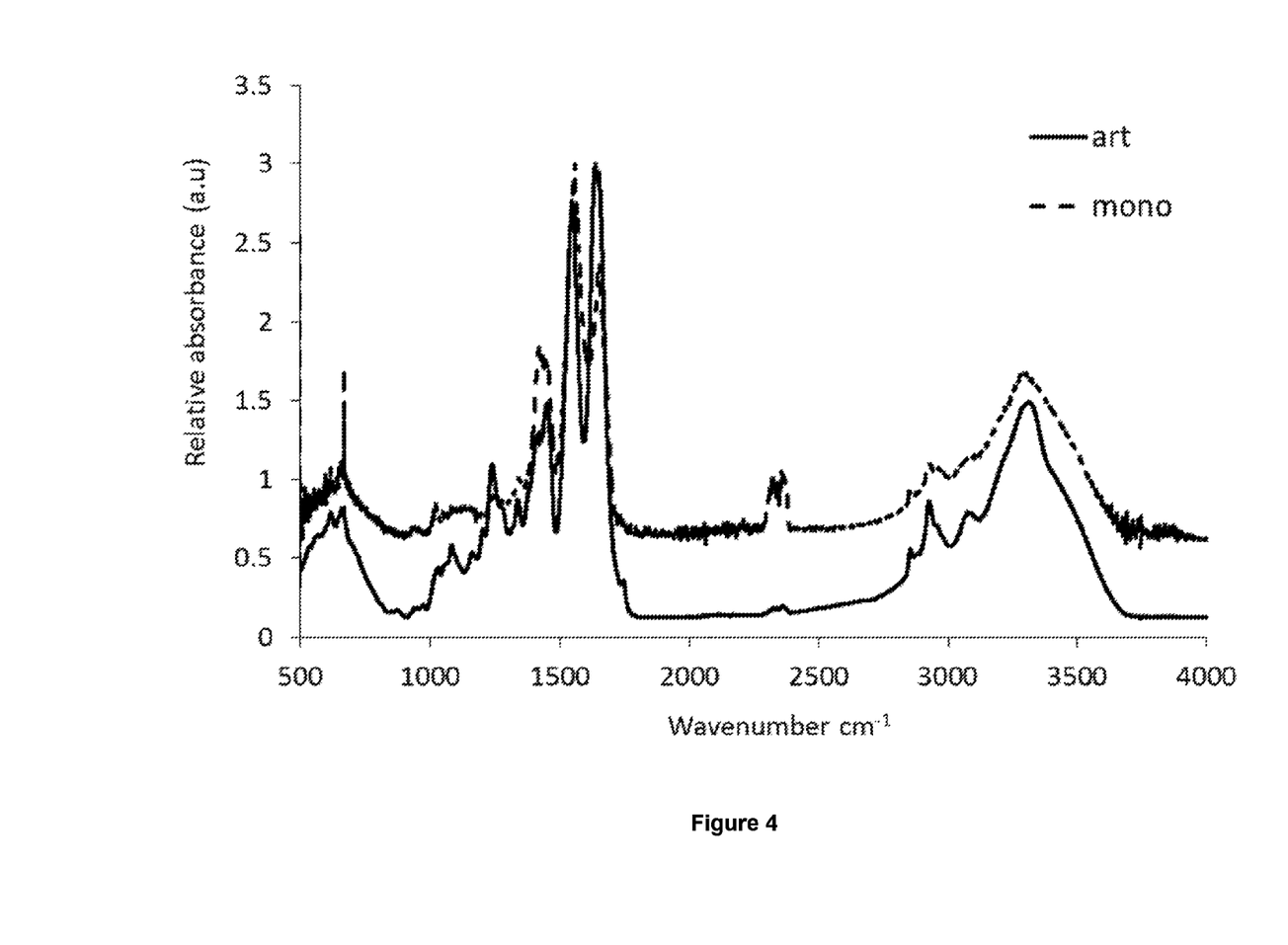
FIG. 4 shows the FTIR spectrum of bovine collagen either extracted using the process of the invention (mono) or extracted using methods of the art (art).
Figure 5:
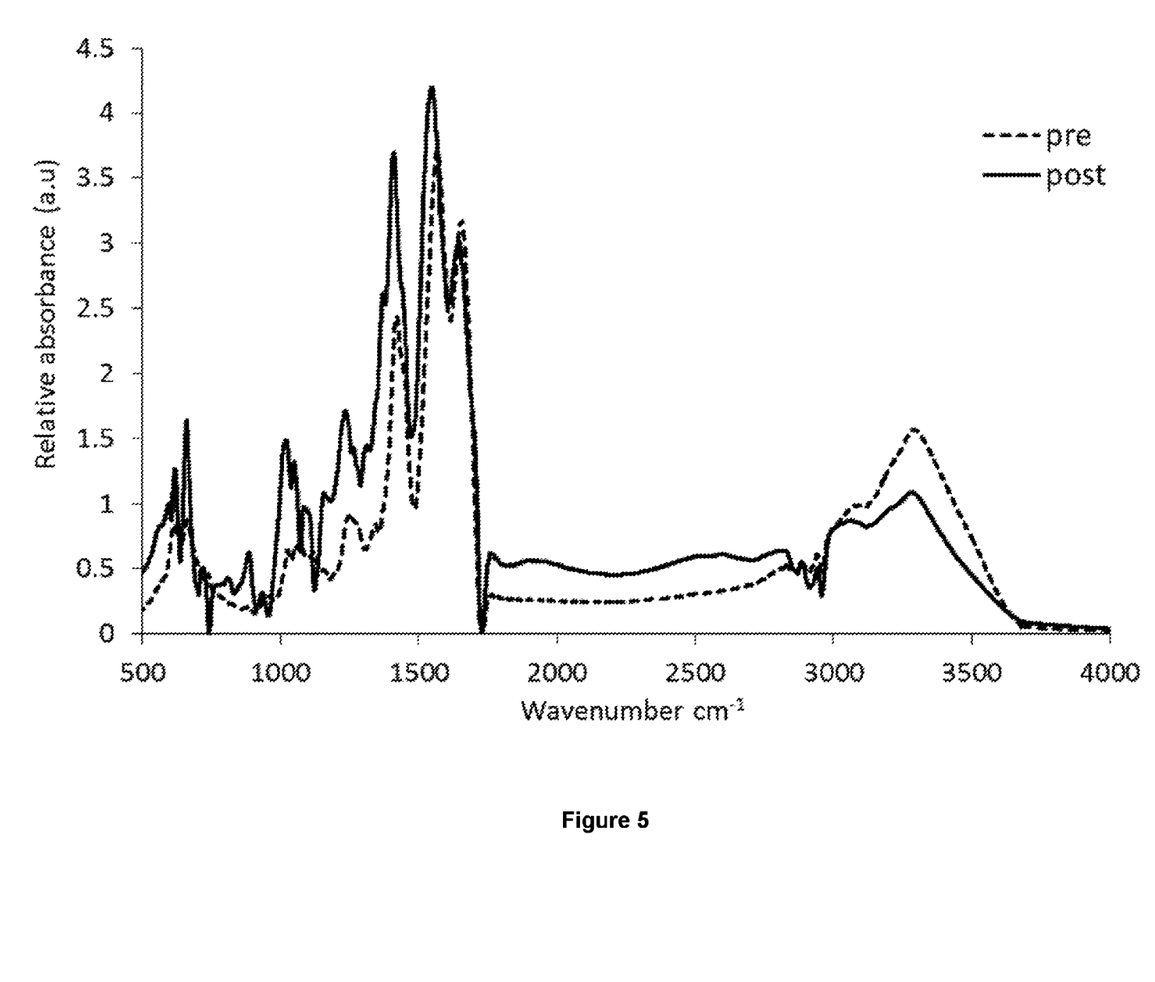
FIG. 5 shows the FTIR spectrum of the jellyfish collagen extracted using the method of the invention using before (pre) and after (post) electrospinning.

A "peak intensity" or "absorption value" as referred to herein is the maximum absorption value at any wavenumber within the specified regions of an FTIR spectrum. A "peak intensity" or absorption value" can be determined from a FTIR spectrum using peak detection or peak peaking software that involves the determination of absorption at specific wavenumbers in a spectrum. Peak detection can be used for the qualitative and quantitative analysis of sample substances. The peak detection software can be used to ascertain whether a peak is in fact a true peak within an FTIR spectrum. Peak picking can also be performed manually. In an automated software package, the software may first calculate the first and second order derivatives at wavenumbers of the spectrum and use these results to ascertain at which wavenumbers in a spectrum the first order derivative changes from a positive to a negative. These positions are considered to be peak candidates. Peak candidates are discarded if the absorbance value does not meet a threshold value, where the threshold value is the minimum absorbance value within a spectrum considered not to be noise. Then, the difference in the first derivative value between each candidate point and the points before and after is calculated, and the points for which the value of this difference does not attain the specified noise level, these candidate peaks are discarded. For the remaining peak candidates, at wave numbers surrounding these candidate points, wavenumbers are searched for where the first order derivative changes from a negative to a positive and where the second order derivative is negative. If such points are found, these are considered to be the valley surrounding the candidate peak. Then, the two valleys can be joined to form baselines and the heights (i.e. the absorption value) and area of the peak can be calculated. For manual peak picking, the absorption value or peak intensity may simply be detected by ascertaining the absorption value or peak intensity at peak maxima. Manual or automated peak picking can also be used to ascertain the relative absorption value of a peak, where a relative absorption value is defined as the absorption value at a particular peak (i.e. wavenumber) when the total absorption intensity is normalised to a value of 1, or any other arbitrary value. In some embodiments, the isolated monomeric collagen has the FTIR absorption pattern substantially as shown in FIG. 2.

Methods relating to the preparation of samples for FTIR as well as instructions for performing FTIR and for the processing of data can be found in Fourier Transform Infrared Spectroscopy, Griffiths P R et al; 2007; Wiley-Interscience, which is hereby incorporated by reference.

The terms "substantially" and "about" are used herein to provide literal support for the exact value that the term is used in conjunction with, as well as a value that is near to or approximately the value that the term is used in conjunction with. In determining whether the value is near to or approximately a specifically recited value, the near or approximating unrecited value may be a value which, in the context in which it is presented, provides the substantial equivalent of the specifically recited value. For example, in the context of an FTIR absorption spectrum, "substantially" or "about" may mean that the wavenumber of a peak centre is within 1%, or 2%, or 5% of the wave number of the reference peak maxima. "Substantially" may also mean that the FWHM peak volume or peak height (i.e. the absorbance value) of a peak within the amide I, II or III regions, or the ratio of the FWHM peak volumes within any combination of the amide regions I, II and III is within 1%, or 2%, or 5% of the FWHM peak volume(s) or peak height ratio(s) of those of a reference value. The reference value may be the values calculated from an FTIR absorption spectrum obtained from the monomeric collagen disclosed herein, such as that presented in FIG. 2, for example.

The isolated monomeric collagen can be derived from a vertebrate or invertebrate source of collagen containing matter. In some embodiments, the monomeric collagen is isolated from a source of collagen-containing matter selected from the list consisting of jellyfish, anemone, sea urchin, limpets, mussels, sea cucumbers, bovine, porcine, rodent, equine or finfish. In some embodiments, wherein the collagen is isolated from jellyfish, the collagen is isolated from *Rhizostomas pulmo, Rhopilema esculentum, Rhopilema nomadica, Stomolophus meleagris, Aurelia* sp., *Nemopilema nomurai* or a combination thereof. In some embodiments, the monomeric collagen is isolated from *Rhizostomus Pulmo.*

In some embodiments, the isolated collagen obtainable by the process of the first aspect of the invention may be provided as an aqueous solution, where an "aqueous" solution is any solution in which water is present as the predominant solvent, further where "solvent" has its traditional meaning given by the art. In some embodiments, the aqueous solution is 0.1 M, 0.2 M, 0.3 M, 0.4 M, 0.5 M, 0.6 M, 0.7 M, 0.8 M, 0.9 M or 1 M acetic acid, or about 1×, 2×, 3×, 4×, 5×, or 10× phosphate buffered saline (PBS), for example, such as PBS obtainable from Sigma Aldrich® under Catalogue no. P3813.

In some embodiments, the aqueous solution is "sterile". The term "sterile" is to be understood as meaning a solution free-from microbial contamination and thus compatible for use in cell culture applications. A solution can be sterilised by a number of different means. For example, a solution may be sterilised by autoclave, where the solution is heated to and maintained at a temperature of 121° C. for 15 minutes at about 100 kPa above atmospheric pressure. One skilled in the art would be aware of numerous other methods suitable for sterilising the solutions disclosed herein, for example, by filtration, or treatment with antibiotics.

The collagen may be present in solution at a concentration in the range of 0.01 mg/ml to 600 mg/ml. In some embodiments, the collagen is present in solution at a concentration in the range of about 1 to 10 mg/ml.

According to a third aspect of the invention, there is provided a kit comprising: (a) the collagen obtained according to the first aspect of the invention; and (b) a gelling catalyst, wherein the gelling catalyst is an aqueous solution of a pH in the range of pH 4 to pH 9. In some embodiments, the gelling catalyst is of about pH 6.8 to about pH 8.0. In some embodiments, the gelling catalyst is an aqueous solution of about pH 7.4. In some embodiments the gelling catalyst is selected from the list consisting of 1×, 2×, 3×, 4×, 5×, or 10×PBS or 1×, 2×, 3×, 4×, 5×, or 10× Hank's Balanced Salt Solution. As defined herein a "gelling catalyst" is any solution which can promote the formation of a collagen hydrogel. A collagen "hydrogel" consists of a network of soluble collagen fibres that are prevented from dissociating by polymer entanglement and/or covalent cross-linking. They can also be formed from colloidal suspensions. Typically, hydrogel formation is catalysed by diluting the collagen to a concentration of from 1 to 10 mg/ml in a solution with a pH in the range of from pH 6.8 to pH 8.0 and incubating at a temperature of from 4° C. to 25° C. for about 5 to 60 minutes. The exact conditions employed for promoting hydrogel formation will be dependent on the collagen molecule forming the basis of the hydrogel and will be evident to the person skilled in the art. Suitable conditions are disclosed in GB1615205.0, which is hereby incorporated by reference.

In some embodiments, the collagen is provided in a lyophilised form. The term "lyophilised" is to be understood as meaning stable preparation of a biological substance generated by rapid freeze-drying and dehydration of a frozen collagen solution under high vacuum. When the collagen is provided in a lyophilised form, the kit may further comprise a reconstitution buffer, said reconstitution buffer being an aqueous solution of a pH in the range of about pH 1 to pH 6.5 or in the range of about pH 8 to pH 14. The reconstitution buffer is intended for dissolving the lyophilised collagen. In some embodiments, the reconstitution buffer is designed to disfavour collagen fibril formation, i.e. to keep the collagen in a monomeric form. By way of non-limiting example, the reconstitution buffer may be a 0.1 M solution of an acid, wherein the acid is selected from the list consisting of acetic acid or hydrochloric acid.

In some embodiments, the volume of reconstitution buffer is sufficient to dissolve the collagen to a concentration of in the range of about 1 mg/ml to about 10 mg/ml.

In some embodiments, the reconstitution buffer is selected from the list consisting of about 0.1 M, 0.2 M, 0.3 M, 0.4 M, 0.5 M, 0.6 M, 0.7 M, 0.8 M, 0.9 M or 1 M acetic acid, or about 1×, 2×, 3×, 4×, 5×, or 10×PBS, wherein the PBS is at a pH in the range of pH 6 to pH 9. In some embodiments, the PBS is in a pH in the range of pH 7.0 to pH 7.5.

In some embodiments, the kit further comprises a cross-linking agent. As defined herein, the terms "cross-linker" or "cross-linking agent" are used interchangeably and refer to a reactive chemical compound that can, under certain conditions, form covalent linkages between two independent molecules. In the context of the present invention, a cross-linking agent is used to covalently link two independent collagen molecules. In some embodiments, the collagen molecules to be cross-linked are in the form of collagen fibres. In some embodiments, inter-fibril cross-linking takes place. Cross-linking agents are typically composed of two or more reactive functional groups linked together by a hydrocarbon chain. The two or more functional groups do not necessarily have to be the same. The length of the hydrocarbon chain can also be varied to control the distance between the functional groups. The exact length of the hydrocarbon chain in the context of the present invention is not intended to be limiting. Furthermore, the type of reactive functional group of the cross-linking agent is not particularly limiting. It is envisaged that any cross-linking agent known to cross-link under the conditions within which collagen fibrils are formed would be a suitable cross-linking agent for use in the invention. In certain applications, it may be desirable to use a cross-linking agent that is non-toxic to cells. In some embodiments, the cross-linking agent is selected from list consisting of genipin, 1,4-BDDGE, or mucochloric acid, glutaraldehyde, 1-ethyl-3-(3-dimethylaminopropyl)carbodiimide and a combination thereof.

In a fourth aspect of the invention, there is a process for the production of a three-dimensional collagen matrix scaffold, comprising the preparing a monomeric collagen spinning solution by first lyophilising the monomeric collagen defined in the first aspect of the invention or obtainable from the process of the third aspect of the invention, and dissolving the lyophilised monomeric collagen in an organic solvent. This is referred to as step (a) of the fourth aspect of the invention.

In some embodiments, the organic solvent is selected from the list consisting of dimethylformamide, dimethylsulphoxide, tetrandyrofuran, chloroform, ethyl acetate, dichloromethane, methanol, ethanol. hexafluoroisopropanol, acetic acid, hydrochloric acid and a combination thereof. In some embodiments, the organic solvent is acetic acid. In some embodiments, the monomeric collagen within the spinning solution is in the range of about from 1 wt % to 60 wt %.

Subsequent to step (a), the fourth aspect comprises spinning the spinning solution by using an electro-spinner and volatilizing the organic solvent at the same time to form a 3D collagen scaffold. This is referred to as step (b) of the fourth aspect of the invention.

In some embodiments, step (b) is carried out under the following conditions: temperature of from 0° C. to 55° C.; voltage of from 7 to 90 kV; relative humidity of from 0.5 to 85%; spinning distance of from 10 cm to 40 cm; flow rate of from 0.01 to 30 ml/h; and an internal spinning tip diameter of about 6 G (5.16 mm) to 25 G (0.556 mm). In some embodiments, the temperature is of from 0° C. to 55° C. In some embodiments, the voltage is about from 4 kV to 37 kV. In some embodiments, the spinning distance is 25 cm. In some embodiments, the flow rate is about 0.75 ml/hour.

Further to the embodiments disclosed herein, the electrospinning process may be performed using a needless electrospinning device. Such a device requires different parametric values in order to achieve optimal electrospinning of the collagen disclosed herein. For example, a needless electrospinning device may be operated under the following conditions: 0° C. to 55° C.; voltage of from 7 to 90 kV; relative humidity of from 0.5 to 85%; spinning distance of from 10 cm to 40 cm; flow rate of from 0.01 to 30 ml/h.

In a fifth aspect of the invention, there is provided a three-dimensional collagen scaffold obtainable by electrospinning the collagen obtainable from the process of the first aspect of the invention. As used herein, the term "scaffold" is to be understood to be a columnar or porous structure with fairly uniform pore sizes of between 200 μm to 400 μm.

In a sixth aspect of the invention, there is provided a three-dimensional collagen scaffold obtainable by the process of the fourth aspect of the invention.

In a seventh aspect, there is provided an electrospun collagen scaffold characterised in having a relative peak ratio of at least 1.05, wherein the greatest peak intensity in a peak region of 1670 $cm^{-1}$ or less and 1630 $cm^{-1}$ or more in an FTIR spectrum is the denominator, and the greatest peak intensity in the peak region of 1575 $cm^{-1}$ or less and 1515 $cm^{-1}$ or more in an FTIR spectrum is the numerator.

In some embodiments, the collagen fibres of the collagen scaffold have an average fibre diameter in the range of from 20 nm to 3000 nm.

In an eighth aspect of the invention, there is provided the use of the collagen obtainable by the process of the first aspect of the invention or the collagen scaffold of the fifth, sixth, or seventh aspect of the invention, in the manufacture of a wound healing dressing. In another aspect, there is provided a wound healing dressing incorporating the collagen scaffold of the invention.

A wound in the context of the present invention refers to an injury to living tissue caused by a cut, blow, or other impact, that typically results in the skin being cut or broken. A wound dressing is typically designed to cover the wound to provide a sterile environment during healing. A wound dressing may expedite the healing process, for instance when medical agents are applied to the wound dressing on the surface to be contacted to the skin. Collagen is one such reparative agent and acts to attract cells such as fibroblasts and keratinocytes to the wound site in order to enhance tissue repair. The collagen or collagen scaffold can also provide structural support for new tissue growth.

Collagen or collagen scaffolds incorporated into wound healing dressings are capable of promoting connective tissue deposition angiogenesis, reepithelialization, and fibroplasia. The wound healing devices can also serve as effective and sustained delivery systems for therapeutic agents, such as antimicrobial agents or human growth factors and/or hormones to promote the regeneration of wound damaged tissue.

Typically, wound healing dressings that incorporate electropsun collagen scaffolds comprise multiple nanofibrous layers. The wound healing dressing may have a first nanofibrous layer that is an outer supporting layer that may be hydrophobic in nature. The dressing may have a second layer that comprises the collagen or collagen scaffold of the invention. The second layer may be the wound contacting layer. Alternatively, the second layer may be coated with a third layer that is hydrophilic in nature and may further comprise additives useful in the reparation of wound-damaged tissue.

Methods and techniques required for the construction of the wound healing dressings and the composition of the various layers within the wound healing dressings will be well known to the skilled artisan, including those techniques and compositions disclosed in D. Brett (2008). A review of collagen and collagen based wound dressings. *Wounds;* 20(12), which are hereby incorporated by reference.

In another aspect, there is provided a three-dimensional cell culture scaffold comprising the collagen obtainable by the process of the first aspect of the invention.

Collagen scaffolds are rapidly becoming an essential component of modern cell culture techniques. They enable the growth of cells in a 3D lattice more reminiscent of their in vivo environment. The ability to culture cells in vitro in an in vivo environment has obvious benefits for the study of cell biology. Collagen scaffolds can also be used as tissue engineering scaffolds for the manufacture of tissues in vitro for surgical transplantation. Suitable collagen scaffolds include the electrospun collagen scaffolds disclosed herein and three-dimensional collagen hydrogels, such as those disclosed in GB1615205.0. The collagen obtainable by the process of the first aspect of the invention or kit of the invention can be used to manufacture a collagen hydrogel by employing the methods disclosed in GB1615205.0. The three dimensional scaffolds may be used for culturing cells in vivo or in vitro. In some embodiments, the scaffolds are used to culture cells in vitro. In some embodiments, the scaffolds are used for tissue engineering.

In some embodiments, the scaffolds are used for the engineering of a tissue selected from the list consisting of corneal shields, neurons, liver, heart, skin, cartilage, muscle, dental tissue, kidney, vasculature tissue, lung, gastrointestinal tissue and a combination thereof. The exact cell culture conditions, including the additives that are required for the stimulating the development of specific tissues, organs or cell types will vary depending of the tissue to be engineered.

The invention is illustrated by the following non-limiting examples

EXAMPLES

Materials and Methods

Jellyfish was fished from the South Wales coastline, washed to remove impurities and frozen. This was then defrosted and again washed to remove any non-jellyfish material. The weight of the jellyfish was recorded and the material blended to achieve a smooth paste of material.

Bovine insoluble collagen material from calf tendon was purchased from Sigma and hydrated in deionised water for 24 hours.

Limpets of the species *Patella vulgate* were collected off the South Wales coastline and de-shelled and washed to remove debris. The soft tissue was blended to achieve a smooth paste of material.

Mussels of the species *Mytilus edulis* were purchased from local suppliers de-shelled and washed to remove debris. The soft tissue was blended to achieve a smooth paste of material Dried sea cucumber powder of the species *Holothuria edulis* was purchased from providers of such materials and hydrated in DI water for 24 hours Example 1—Collagen Extraction Process Jellyfish and other marine derived materials described in Materials and Methods were treated individually using the same process by first immersing in a 0.1M NaOH solution at 4° C. for 3 days with constant mixing and circulation to break down any non-collagenous material. The solution was then diafiltrated using a 50,000 NMWC hollow fibre size exclusion membrane system to remove NaOH until <8.0 was achieved. Once complete, the solution was subjected to 0.5M Acetic acid treatment for 3 days at 4° C. with constant stirring and circulation to dissolve the collagen. The collagen solution was then passed through a 0.2 µm filter, surprisingly enabling a substantially purified solution of monomeric collagen to be obtained as the filtrate. The retentate comprising residual insoluble collagens was returned to the acetic acid treatment step.

The non-monomeric collagen was again diafiltered until a pH of >6 was achieved. This solution was then subjected to a further two 0.5M acetic acid treatments, each for 3 days at 4° C. with constant stirring and circulation. After each acid cycle, a further 0.2 µm filtration step was performed to separate soluble monomeric collagen of approximately 100 kDa. Once complete, the final concentrated non-monomeric collagen solution was collected.

Vertebrate (Bovine) material was subjected to an initial 0.5M acetic acid treatment for 3 days at 4° C. with constant stirring and circulation to dissolve the collagen. This was then subjected to diafiltration using 50,000 NMWC hollow fibre size exclusion membranes until a pH>6.0 was achieved. This was then subjected to a further two treatments with 0.5M acetic acid for 3 days at 4° C. with constant stirring and circulation. After each acid cycle, the collagen solution was subjected to a 0.2 µm filtration step, allowing the monomeric collagen to be obtained as the filtrate, while residual insoluble collagens forming the retentate were returned back into the acetic acid treatment step.

The non-monomeric collagen was again diafiltered until a pH of >6 was achieved. This solution was then subjected to a further two [2] treatments with 0.5M acetic acid, each for 3 days at 4° C. with constant stirring and circulation. After each acid cycle, a 0.2 µm filtration step separated out monomeric collagen of approximately 100 kDa. Once complete, the monomeric collagen solutions were concentrated using a 50,000 NMWC hollow fibre size exclusion membranes.

This experiment shows that the method can effectively purified collagen in a monomeric conformation.

Example 2—SDS-PAGE Analysis

Samples of isolated collagen obtained from the process of example 1 were diluted 1:10 high purity water (HPW). Samples were vortexed for 3 seconds, partially denatured in a heat block at 70+/−5° c. for 10 minutes, allowed to cool, and vortexed for a further 3 seconds. 45 µl of each sample was added to a clean Eppendorf tube. NuPAGE LDS Sample Buffer 4× (Cat #: NP0007) was gently shaken and 15 µl was added to each Eppendorf tube to give a total volume of 60 µl which were vortexed for 5-10 seconds. 50 ml of NuPAGE 20× Tris-Acetate SDS Running Buffer (CAT #: LA0041) was added to 950 ml HPW in a large beaker and mixed gently with a magnetic stirrer. The electrophoresis tank and electrode assembly were rinsed with HPW. A 3-8% Tris Acetate gel cassette (NuPAGE Novex 1.0 mm, 10 well Cat #: EA0375BOX) was used and the manufacturer's instructions followed. 15 µl of each sample was loaded into each well. 5 µl of protein molecular weight marker (Precision Plus Protein™ Unstained Standards Cat #: 161-0363) per well was sufficient. The loading guides on the cassette were used to locate the wells. The electrode assembly was attached and the gel ran at 150 v for approximately 70 minutes until the dye had almost reached the bottom of the gel. Gel cassettes were then removed and the gel carefully removed from its plastic casing before being washed for 5 minutes with approximately 200 ml of HPW on the rotating platform 3 times. The gel is then soaked in Biosafe coomassie G-250 stain (Bio-Rad, Cat #: 161-0786) for a minimum of 1 hour and destained in HPW overnight after a further 3 washes for 5 minutes each in approximately 200 ml of HPW on the rotating platform.

Figure 1:
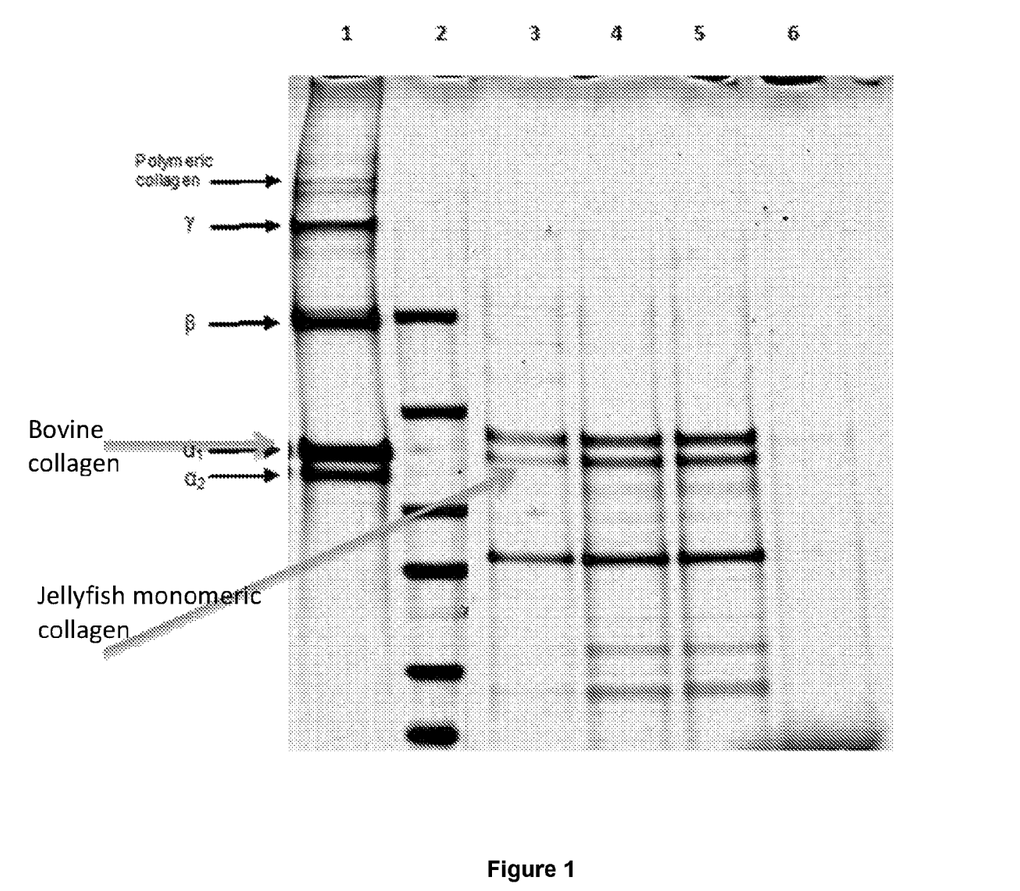
FIG. 1 shows the SDS-PAGE analysis of the collagen extraction process. Lane 1 shows a sample of bovine collagen, lane 2 shows high molecular weight protein marker, lanes 3 to 5 4 show 100 μL, 200 μL and 400 μL samples of the jellyfish collagen obtained by the process disclosed herein. All SDS samples contain 0.2 mg/mL protein by biuret test.

The SDS-PAGE analysis shows that using the extraction method of example 1 monomeric collagen can be obtained (FIG. 1, lanes 3 to 5). This is in comparison to current commercially available collagens, where a large proportion of collagen is present in a higher order form (e.g. β or γ collagen FIG. 1, lane 1).

Example 3—Electrospinning

A solution of 90% acetic acid from Glacial in DI was produced and chilled to 4° C. Following this, the dried monomeric collagen samples were weighed and added to an appropriate amount of acetic acid to produce a 25% collagen solution (w/w). This was vortexed thoroughly until the collagen was fully dissolved and a consistent liquid was produced and was stored at 4° C. to prevent the collagen from denaturing.

The electrospinning apparatus was set up using aluminium foil as the grounding target and was connected to ground. The syringe pump was set up to the correct diameter for a BD Plastipak® 10 ml needle and an 18 G blunt tipped needle was used. These were rinsed with deionised water, followed by a blank 90% acetic acid solution prior to the solution being taken into the syringe.

The syringe pump was set to use a flow rate of 0.75 mL per hour. The distance from needle tip to collector was 25 cm and a voltage of 20 kV was used. Voltage was applied when a droplet had formed at the tip of the needle and flow was maintained so volume of the droplet did not increase or reduce. An acetic acid bath was placed in the electrospinning unit to prevent gelation of the droplet during periods of prolonged electrospinning.

The mat produced was then sampled and coated in a 5 nm layer of chromium before being examined by scanning electron microscopy (SEM) using a Hitachi S4800 FEG-SEM at an acceleration voltage of 10 kV and emission current of 9 μA. Micrographs were taken with a magnification of 1500× for fibre diameter measurements which were analysed using ImageJ software. The diameter of fibres was calculated with three sets of 30 measurements per sample and averaged. The fibres produced by monomeric collagen electrospinning at 25%-60% (w/v) in 90% AcOH (w/w) produced fibres with an average diameter of 646 nm SD±120.8 nm.

Monomeric bovine collagen was electrospun in a 25% concentration at a distance of 15 cm and 17 kV with an 18 G needle. Fibres were imaged using SEM and images were analysed for fibre diameters using image J software. The average fibre diameter was 83.7 nm+−27.0 nm, approaching the theoretical minimum fibre diameter obtainable by electrospinning.

Example 4—FTIR Analysis

Collagen samples were examined using a Perkin Elmer FTIR/ATR device using a soft tip. A small volume of solution was placed on the diamond stage and allowed to dry. The samples were then tested using a scan range from 4000-400 $cm^{-1}$. Once background correction was carried out, the data normalised and was analysed using the Spectrum software and compared between samples to give a percentage similarity.

Samples were compared based on their calculated % homology which should be >98% for them to be defined as chemically identical. Furthermore, the ratio of amides I, II & III were examined to observe any changes in alpha-helical secondary protein structure.

A reduction of an amide band can indicate a change in the secondary structure of the collagen. In particular a reduction of the amide III region indicates an unravelling of the alpha helical structure of collagen. Electrospinning of monomeric collagen shown in the example spectra indicates that the amide III region has not been diminished by the electrospinning as has been shown to occur when the solvents hexafluoropropanol or trifluoroethanol are used.

The results of the peak picking analysis within the amide I region are shown in Table 1. These values were determined from FTIR spectrum collected for samples of jellyfish collagen produced by the method of the invention (mJFC), jellyfish collagen of the art (aJFC), an electrospun collagen scaffold obtained by electrospinning the jellyfish collagen of the invention (emJFC), bovine collagen produced by the method of the invention (mBC) and bovine collagen of the art (aBC).

The relative peak ratios were calculated by determining the greatest peak intensity in the FTIR wavenumber regions of 1515 to 1575 $nm^{-1}$ (amide II region) and 1630 to 1670 $cm^{-1}$ (amide I region) from FTIR spectrum of mJFC, aJFC, emJFC, mBC and aBC. The greatest peak intensity in each amide region is shown in Table 2, along with the relative peak ratio, which is calculated by dividing the greatest peak intensity in the amide II region with the greatest peak intensity in the amide I region.

The results show that the relative peak ratio of both jellyfish and bovine collagen extracted using the method of the invention are greater than one, whereas collagens of the art have a relative peak ratio of less than one.

TABLE 1 analysis of relative intensities (absorption values) at various FTIR wavenumbers in the indicated spectra

| Expected λ (±2 $cm^{-1}$) | mJFC | emJFC | aJFC | aBC | mBC | Corresponding Vibration |
|---|---|---|---|---|---|---|
| 1690 | 1.8035 | 1.8035 | 1.5287 | 0.9978 | 1.2538 | Parallel β-Sheets |
| 1680 | 2.0959 | 2.0959 | 1.9636 | 1.4175 | 1.5836 | Anti-Parallel β-Sheets |
| 1668 | 2.5195 | 2.5195 | 2.5355 | 2.1582 | 1.9593 | B-Turns |
| 1658 | 2.8229 | 2.8229 | 2.9415 | 2.7337 | 2.1756 | A-Helix |
| 1647 | 2.9997 | 2.9997 | 3.0811 | 2.9455 | 2.2997 | Unordered |
| 1638 | 2.9628 | 2.9628 | 2.9231 | 2.9599 | 2.0732 | Triple Helix |
| 1625 | 2.7993 | 2.7993 | 2.4492 | 2.5582 | 1.8461 | Parallel β-Sheets |
| 1612 | 2.5683 | 2.5683 | 1.8777 | 1.7391 | 1.741 | B-Turns |

TABLE 2 relative peak intensities

|  | mJFC | aJFC | emJFC | mBC | aBC |
|---|---|---|---|---|---|
| max Intensity amide I | 3.173 | 3.0905 | 3.0151 | 2.3561 | 3 |
| max Intensity amide II | 3.7231 | 2.6429 | 4.1997 | 2.9988 | 2.7206 |
| relative peak ratio | 1.173369 | 0.855169 | 1.392889 | 1.272781 | 0.906867 |

The invention claimed is:

1. A process for the extraction of collagen from collagen-containing matter derived from jellyfish, comprising the steps of:

(a) incubating the collagen-containing matter in an acidic solution for at least 1 h at a temperature in the range of about 0° C. to about 37° C. to form an incubant;

(b) diafiltrating the incubant from step (a) to substantially purify solubilised collagen within the incubant, thereby forming a retentate; and (c) separating the soluble and insoluble matter of the retentate obtained from step (b) to remove the remaining insoluble matter, wherein the separation is performed by filtration;

and wherein the process further comprises passing the substantially pure collagen solution obtained from step (c) through a 0.4 m filter to obtain a first filtrate, and then passing that first filtrate through a 0.2 m filter to obtain a second filtrate, wherein the second filtrate is a substantially pure monomeric collagen solution.

2. The process according to claim 1, wherein step (a) is performed at a temperature in the range of about 0° C. to about 22° C.

3. The process according to claim 2, wherein step (a) is performed at a temperature in the range of about 2° C. to about 6° C.

4. The process according to claim 1, wherein step (a) is performed for in the range of about from 1 to 168 h.

5. The process according to claim 1, wherein step (b) is performed using a hollow fibre membrane with a molecular weight cut-off of 50 kDa.

6. The process according to claim 1, wherein in step (c) the filtration is performed by passing the retentate through a filter having a pore selected from the group consisting of 1 µm and 20 µm and a combination of 1 µm and 20 µm thereof.

7. The process according to claim 1, wherein the jellyfish is selected from the group consisting of *Rhizostomas pulmo, Rhopilema esculentum, Rhopilema nomadica, Stomolophus meleagris, Aurelia* sp., *Nemopilema nomurai* and a combination thereof.

8. The process according to claim 1, further comprising the steps of, prior to step (a), (i) incubating the collagen-containing matter in a strong base for from 4 h to 96 h at a temperature in the range of from 2° C. to 37° C. to dissolve non-collagenous material;

(ii) diafiltering the incubant of step (i) to remove the dissolved non-collagenous material thereby forming a retentate; and (iii) retaining the retentate from step (ii) for use in step (a).

9. The process according to claim 8, wherein the strong base is from 0.1 M or to 1 M sodium hydroxide.

10. The process of claim 1, further comprising the step of:

(d) repeating steps (a) and (b) on the insoluble matter obtained from step (c).

* * * * *